(12) United States Patent
Hayman et al.

(10) Patent No.: US 8,777,615 B2
(45) Date of Patent: Jul. 15, 2014

(54) DENTAL PROPHYLAXIS DEVICES

(76) Inventors: Robert Hayman, Los Angeles, CA (US); Rene Robert, West Warwick, RI (US); Dave Pakula, Providence, RI (US); Andy Marsella, Boston, MA (US); Jorah Wyer, Providence, RI (US); Christopher Quan, Houston, TX (US)

( * ) Notice: Subject to any disclaimer, the term of this patent is extended or adjusted under 35 U.S.C. 154(b) by 215 days.

(21) Appl. No.: 12/210,579

(22) Filed: Sep. 15, 2008

(65) Prior Publication Data
US 2009/0081610 A1    Mar. 26, 2009

Related U.S. Application Data

(60) Provisional application No. 60/972,734, filed on Sep. 14, 2007.

(51) Int. Cl.
*A61C 1/08* (2006.01)
(52) U.S. Cl.
USPC ........................... 433/126; 433/116; 433/125
(58) Field of Classification Search
USPC .................................. 433/114, 116, 125–126
See application file for complete search history.

(56) References Cited

U.S. PATENT DOCUMENTS

| | | | |
|---|---|---|---|
| 1,534,817 A * | 4/1925 | Thiedemann et al. ........ 433/116 |
| 3,471,668 A | 10/1969 | Wilkes | |
| 3,570,719 A | 3/1971 | Schiff | |
| 3,579,835 A | 5/1971 | Levenson | |
| 3,977,084 A | 8/1976 | Sloan | |
| 4,014,099 A | 3/1977 | Bailey | |
| 4,021,918 A | 5/1977 | Bailey | |
| 4,123,845 A * | 11/1978 | Fattaleh ......................... 433/99 |
| 4,253,832 A | 3/1981 | Bailey | |
| 4,266,933 A | 5/1981 | Warden | |
| 4,310,310 A | 1/1982 | Bailey | |
| 4,406,621 A | 9/1983 | Bailey | |
| 4,544,356 A * | 10/1985 | Gardella et al. .............. 433/122 |
| 4,601,410 A | 7/1986 | Bond | |
| 5,007,832 A | 4/1991 | Meiler | |
| 5,062,796 A * | 11/1991 | Rosenberg ...................... 433/82 |
| 5,064,098 A | 11/1991 | Hutter | |
| 5,156,547 A | 10/1992 | Bailey | |
| 5,267,860 A * | 12/1993 | Ingram et al. ................. 433/116 |
| 5,286,105 A | 2/1994 | Herold | |
| 5,328,369 A | 7/1994 | Bailey | |
| 5,348,473 A * | 9/1994 | Kivlighan, Jr. ............... 433/114 |
| 5,423,679 A | 6/1995 | Bailey | |
| 5,484,284 A | 1/1996 | Bailey | |
| 5,501,596 A | 3/1996 | Bailey | |
| 5,503,555 A | 4/1996 | Bailey | |
| 5,531,599 A | 7/1996 | Bailey | |
| 5,546,996 A | 8/1996 | Broyles | |
| 5,642,994 A | 7/1997 | Chipian | |
| 5,642,995 A | 7/1997 | Bailey | |
| 5,683,247 A | 11/1997 | Bailey | |

(Continued)

*Primary Examiner* — Eric Rosen
(74) *Attorney, Agent, or Firm* — Frederick W. Tong

(57) ABSTRACT

The present invention is directed to dental prophylaxis devices that improve portability, maneuverability and aid in retaining clean conditions for use on dental patients, particularly to dental handpieces. The present invention is also directed prophylaxis or prophy angles for use with such handpieces. In general, a dental prophylaxis device includes a handpiece and a prophy angle which includes a driven shaft and a prophy cup attached for rotation thereto. The handpiece generally includes a body which houses a rotational source coupled to an output shaft which couples to the driven shaft in the prophy angle via angled gear interfaces on the output shaft and the driven shaft.

13 Claims, 9 Drawing Sheets

(56) References Cited

U.S. PATENT DOCUMENTS

| | | |
|---|---|---|
| 5,692,901 A | 12/1997 | Roth |
| 5,730,595 A | 3/1998 | Bailey |
| 5,871,353 A * | 2/1999 | Pierce et al. ............ 433/84 |
| 5,876,203 A | 3/1999 | Bailey |
| 5,964,590 A | 10/1999 | Loddeke |
| 6,146,140 A | 11/2000 | Bailey |
| 6,203,322 B1 | 3/2001 | Kraenzie |
| 6,321,945 B1 | 11/2001 | Girouard |
| 6,345,734 B2 | 2/2002 | Schalow |
| 6,364,170 B1 | 4/2002 | Anderson |
| 6,371,336 B1 | 4/2002 | Keller |
| 6,382,971 B1 | 5/2002 | Randolph |
| 6,457,609 B1 | 10/2002 | Keller |
| 6,540,113 B2 | 4/2003 | Gardos |
| 6,632,090 B1 | 10/2003 | Randolph |
| 6,921,002 B2 | 7/2005 | Langer |
| 6,932,243 B2 | 8/2005 | Keller |
| 7,017,781 B2 | 3/2006 | Provenza |
| 7,128,246 B2 | 10/2006 | Raia |
| 7,178,692 B2 | 2/2007 | Ophardt |
| 7,422,433 B2 * | 9/2008 | Carron et al. ............ 433/125 |
| 2005/0032022 A1 | 2/2005 | Jaffe |
| 2007/0259307 A1 * | 11/2007 | Quan et al. ............ 433/25 |
| 2007/0281272 A1 * | 12/2007 | Rahbari ............ 433/114 |

* cited by examiner

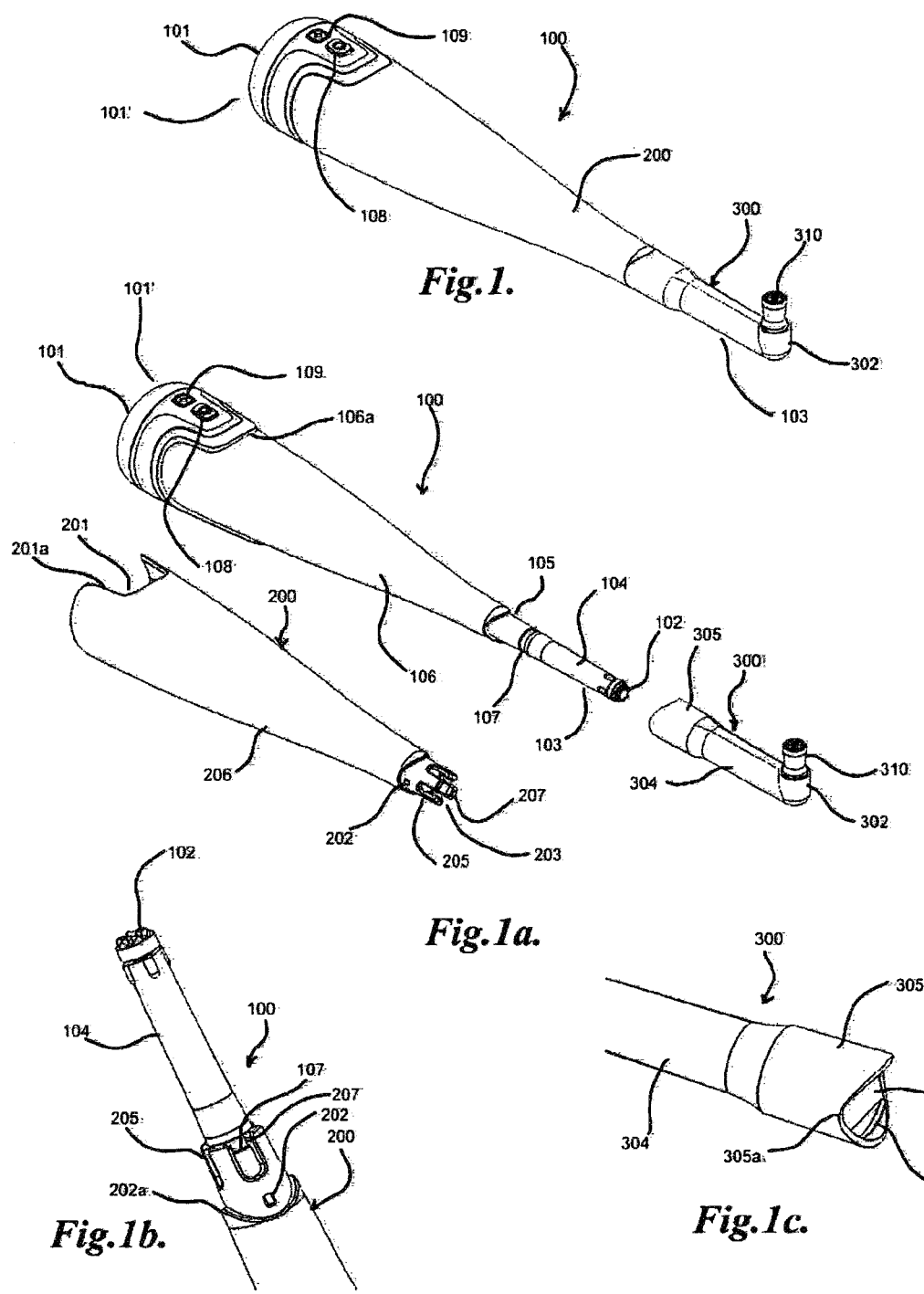

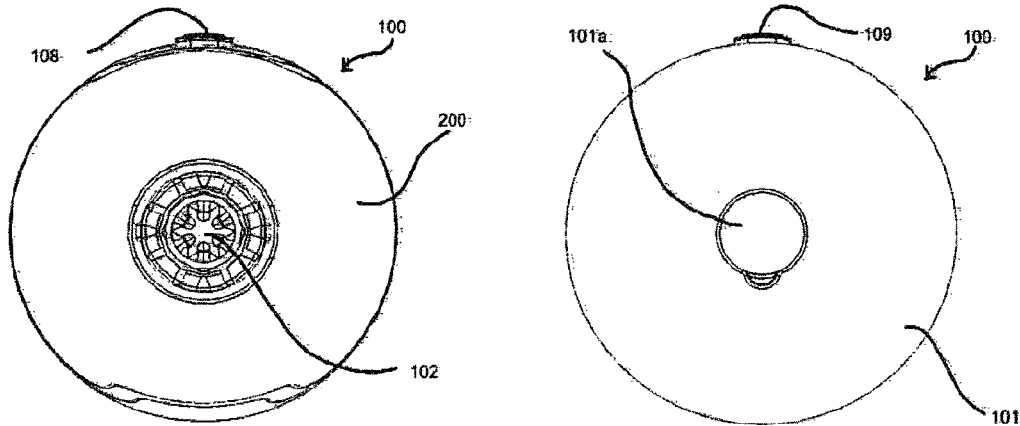
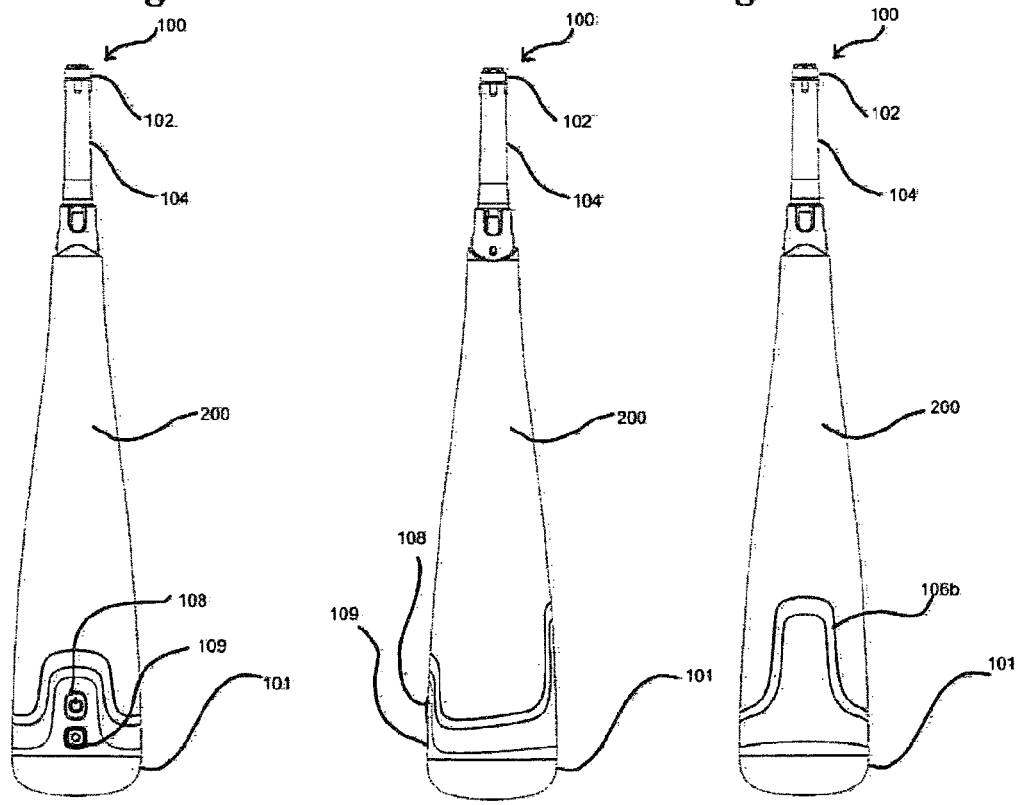
*Fig.1d.*  *Fig.1e.*
*Fig.1f.*  *Fig.1g.*  *Fig.1h.*

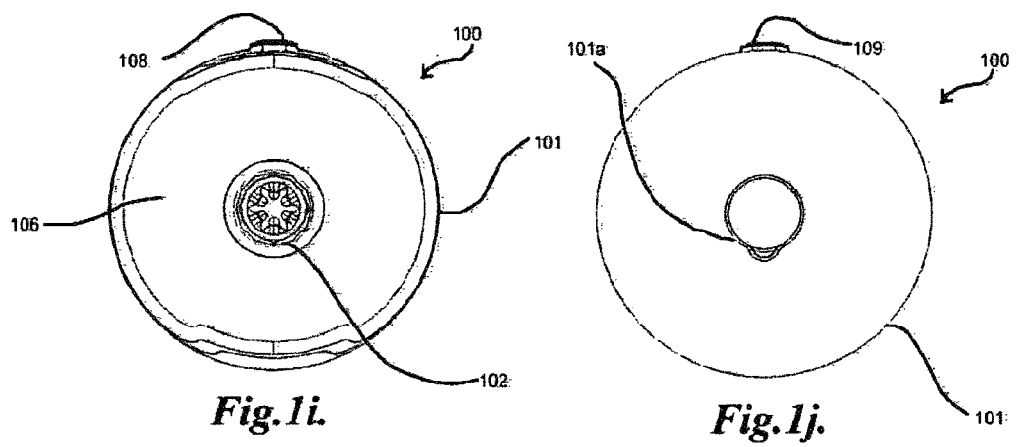
*Fig.1i.*   *Fig.1j.*
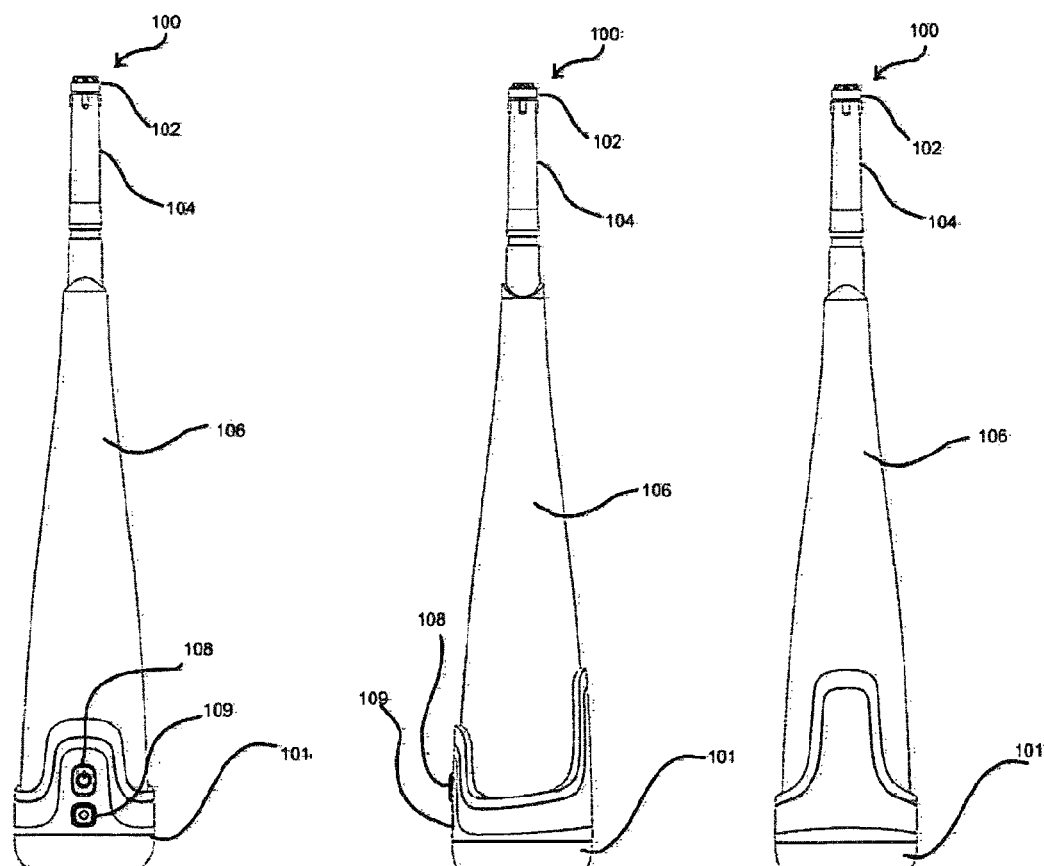
*Fig.1k.*   *Fig.1l.*   *Fig.1m.*

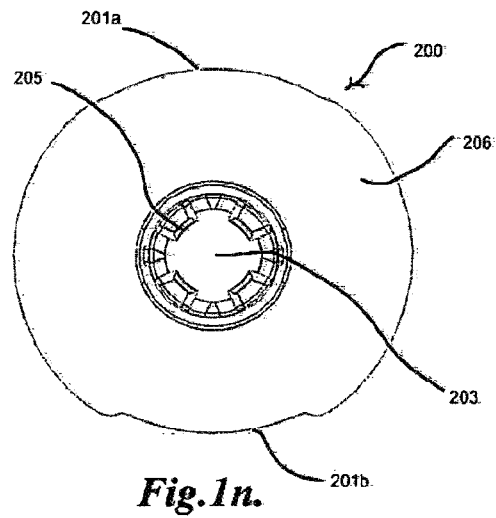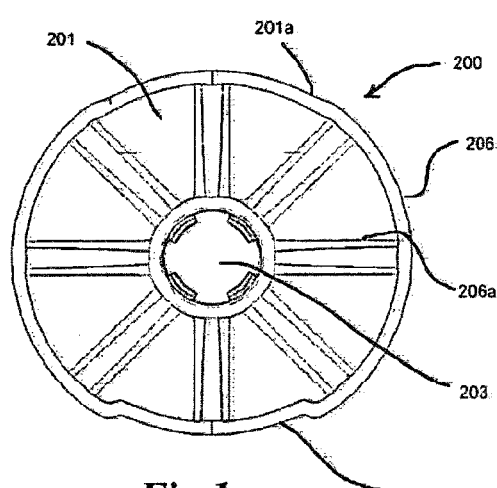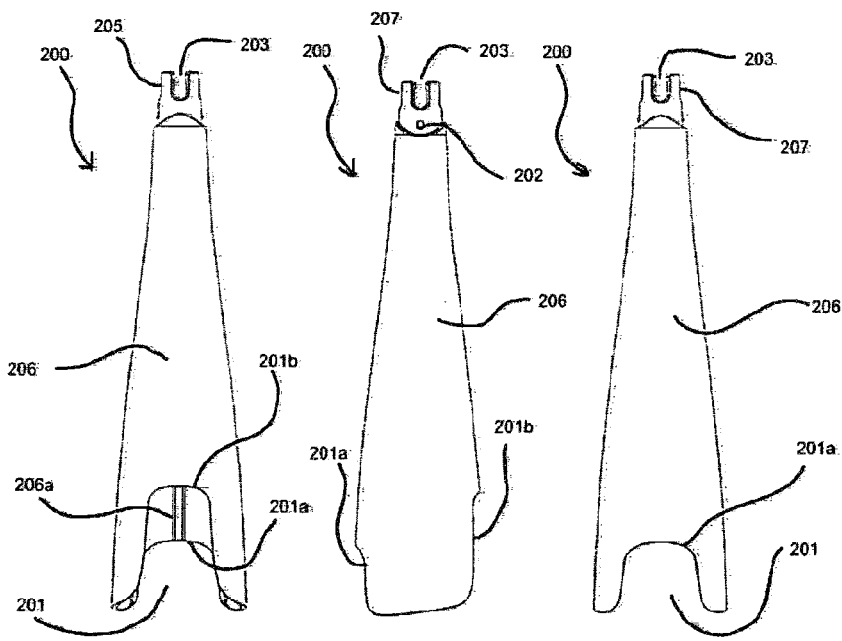

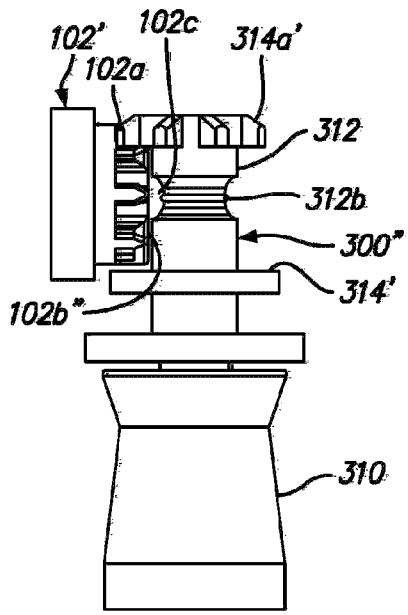
FIG. 3b
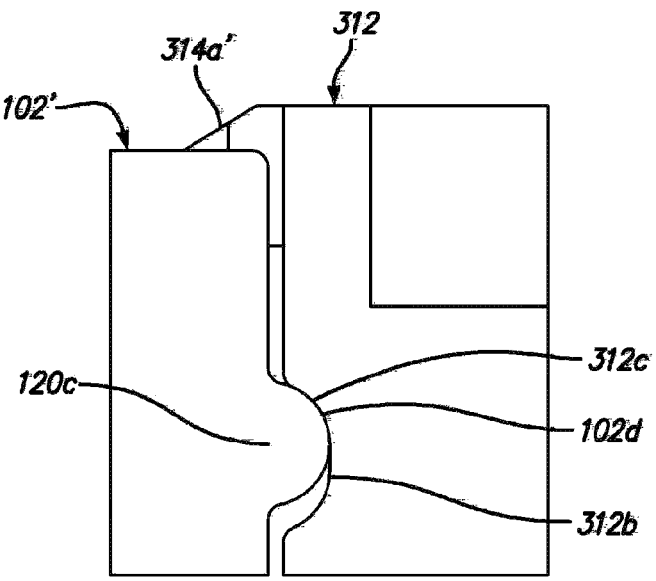
FIG. 3c
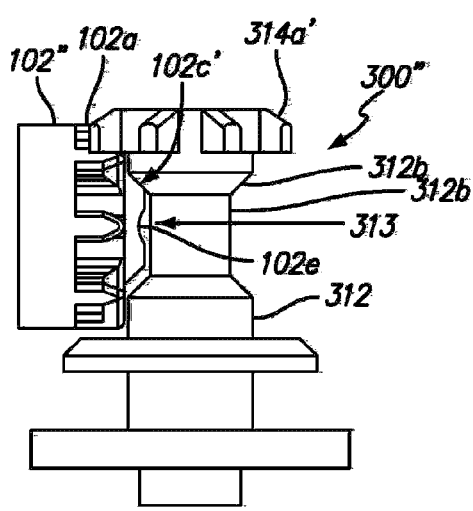
FIG. 3d
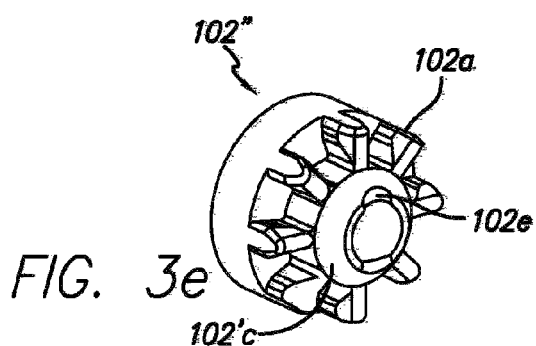
FIG. 3f-1
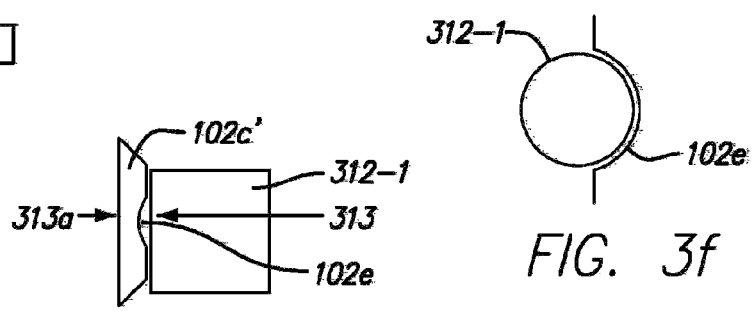
FIG. 3e
FIG. 3f

DENTAL PROPHYLAXIS DEVICES

CROSS-REFERENCE TO RELATED APPLICATIONS

This application claims the benefit and priority of U.S. provisional patent application Ser. No. 60/972,734, filed Sep. 14, 2007, entitled "DENTAL PROPHYLAXIS DEVICES", the entire contents of which are hereby incorporated by reference.

FIELD OF THE INVENTION

The present invention relates to dental devices, particularly to dental prophylaxis devices for cleaning and/or polishing teeth. The present invention further relates to components of dental prophylaxis devices with improved sterility control, operating efficiency and/or manufacturing efficiency.

BACKGROUND OF THE INVENTION

As part of dental hygiene, a patient's teeth are polished by a dental professional during a cleaning visit. Cups are used by dental professionals to carry a polishing paste. The polishing is accomplished by applying a prophylactic polishing paste to the teeth using a small rubber cup, commonly called a prophylaxis or prophy cup. The prophy cup is filled or loaded with a prophylactic polishing paste and the filled cup is held against the surface of a tooth while the cup is mechanically rotated. The force of rotation forces the polishing paste to traverse across the surface of the tooth abrading and polishing it.

The cup is attached to a dental angle, called a prophylaxis or prophy angle. The rotating action is provided by a rotating dental handpiece attached to the prophy angle.

Most dental handpieces utilized with prophy angles are air-driven devices that rely on the compressed air supply found in most dental offices. These handpieces are relatively simple mechanical turbine devices and are convenient in that they are typically reusable and sterilizable by methods such as autoclaving, whereas most electrical devices are less conducive to sterilization due to the high temperatures, high pressures and wet conditions of sterilization. However, these air-driven handpieces must remain tethered by an air line in order to operate. A dental professional may often have to move around the patient and change the position of the dental handpiece in order to reach all of the patient's teeth. This may be troublesome because of the air supply line.

SUMMARY OF THE INVENTION

The present invention is directed to dental prophylaxis devices that improve portability, maneuverability and aid in retaining clean conditions for use on dental patients, particularly to dental handpieces. The present invention is also directed prophylaxis or prophy angles for use with such handpieces.

In general, a dental prophylaxis device includes a handpiece and a prophy angle which includes a driven shaft and a prophy cup attached for rotation thereto. The handpiece generally includes a body which houses a rotational source coupled to an output shaft, which in turn, couples to the driven shaft in the prophy angle via angled gear interfaces on the output shaft and the driven shaft during use and may be easily decoupled when not in use, if desired.

The body of the prophy angle has a generally axial bore and an angled portion, which may also be a second body, similar to traditional angles. The body may be adapted for attachment to a driving source and be adapted for rotatably housing a shaft therethrough, said shaft having attached at one end thereto a cup for use in polishing a tooth or teeth and a second end being adapted for coupling with the driving source for rotation. The driving shaft is not fixedly housed in the body of the angle.

The body may further include other components such as, for example, control circuitry, user controls, indicators, and/or any other appropriate components. In general operation, the user actuates a control to activate the rotational source to rotate the output shaft, which transmits the rotation to the driven shaft via the angled gear interfaces, which in turn rotates the prophy cup for cleaning and/or polishing action of the teeth of a patient. The rotational source may, for example, be an electrically powered motor. The rotational source is generally powered by an appropriate source such as, any energy storage reservoir including a portable energy source, an outside electrical energy source and/or combinations thereof. In general, a battery, removable or non-removable and rechargeable; an electrical fuel cell or a fuel storage reservoir; a capacitor; external electric source; pressurized gas/fluid source; and/or any other appropriate source or combinations thereof may be used.

For example, a battery, capacitor, or other portable energy source may be desirable such that the dental tool 100 may be portable and un-tethered. Portable energy sources may include, but are not limited to, a removable battery or a non-removable rechargeable battery such as a carbon zinc battery, an alkaline battery, a Nickel Metal Hydride battery, a Nickel Cadmium battery, a lithium ion battery, a lithium polymer battery; a capacitor; an electrical fuel cell, or a fuel storage reservoir; and/or any other appropriate portal energy source. It may also be generally more desirable for the energy source to be rechargeable and/or easily replaceable.

The portable energy source may generally be disposed in the housing of the handpiece or be attached thereto. For renewable sources, a charging station may be used and recharging may happen when the instrument is not in use. The charging station may be in a stand for resting the instrument, to be discussed more later.

In one aspect, a dental prophylaxis device also includes a sleeve. In one embodiment, the sleeve may substantially cover a portion of the handpiece such that it may aid in isolating the handpiece from the working space, such as, for example, a patient's mouth. This may generally aid in retaining a clean work environment by reducing the contamination of the handpiece by contact with the patient's mouth and by reducing the introduction of contaminants into the patient's mouth by the handpiece. In general, the handpiece may not be sterilized by methods such as autoclaving due to the sensitivity of the components, such as the portable energy source and/or the rotational source. Further, the high temperature, high pressure and/or high humidity conditions of autoclaving may further contribute to wear and reduction in usage life of the handpiece. The sleeve may thus act as a barrier and it may generally be sterilized or replaced prior to use with a patient.

The sleeve may generally have the form of a hollow shell that may substantially surround a portion of the handpiece. The sleeve may also generally have a first aperture for inserting the handpiece and a second aperture for coupling the handpiece output shaft to the driven shaft of a prophy angle. In some embodiments, the sleeve may contour to the body of the handpiece. This may reduce the overall form size of the dental prophylaxis device and may also aid in providing ergonomic benefits to the user. The handpiece body and/or the sleeve may, for example, be designed for comfortable and secure gripping by a user.

In general, the sleeve may be constructed from a sterilizable and reusable material or combination of materials. Appropriate materials may include, but are not limited to, polymers such as polyetherimides, polycarbonates, acrylics, acetals, polyetheretherketones (PEEK), polypropylenes and polyethylenes, metals such as aluminum, titanium, stainless steel and silver, composite materials such as fiberglass and carbon fiber reinforced plastics, and/or any other appropriate material. The material may generally be autoclavable and reusable for at least a given number of normal use and sterilization cycles. In an exemplary embodiment, the sleeve is made from polyetherimide polymer such as ULTEM® Resin (GE Plastics).

In some embodiments, the sleeve may include coatings capable of eliminating, preventing, retarding or minimizing the growth of microbes, thus minimizing the use of high temperature autoclaving process or harsh chemicals and may increase the kind and number of materials useful as substrates for making such tools or instruments.

The coatings may include chemical anti-microbial materials or compounds that are capable of being substantially permanently bonded, at least for a period such as the useful life sleeve, or maintain their anti-microbial effects when coated with the aid of coating agents, onto the exposed surfaces of the sleeve. In one example, the chemicals may be deposited on the surface of the sleeve by covalent linkage or linkages.

In other embodiments, the coatings may include chemical antimicrobial materials or compounds that may be deposited in a non-permanent manner such that they may dissolve, leach or otherwise deliver antimicrobial substances to a useful field, such as the mouth, during use.

In still other embodiments, the coatings may include sources of anti-microbial agents that may leach and/or release agents in a moist environment or upon contact with moisture. These sources may be incorporated into the substrate materials used for manufacturing the sleeve, or included in the coatings coated on the exposed surfaces of the sleeve. Incorporation of the sources is especially suited to polymeric substrates.

Chemical antimicrobial materials or compounds may include a variety of substances including, but not limited to antibiotics, antimycotics, general antimicrobial agents, metal ion generating materials, or any other materials capable of generating an antimicrobial effect. Chemical antimicrobial materials or compounds may also be selected to, for example, minimize any adverse effects or discomfort to the patient.

The anti-microbial compound may include, but are not limited to, antibiotics, quaternary ammonium cations, a source of metal ions, triclosan, chlorhexidine, and/or any other appropriate compound or mixtures thereof.

In yet further embodiments, antimicrobial activity may be achieved by utilizing the antimicrobial properties of various metals, especially transition metals which have little to no effect on humans. Examples may include sources of free silver ions, which are noted for their antimicrobial effects and few biological effects on humans. Metal ion antimicrobial activity may be created by a variety of methods that may include, for example, mixing a source of a metal ion with the material of a dental instrument during manufacture, coating the surface by methods such as plasma deposition, loosely complexing the metal ion source by disrupting the surface of the dental instrument to form affinity or binding sites by methods such as etching or coronal discharge, and depositing a metal onto the surface by means such as electroplating, photoreduction and precipitation. The sleeve surface may then slowly release free metal ions during use that may produce an antimicrobial effect.

In some embodiments, the source of metal ions may be an ion exchange resin. Ion exchange resins are substances that carry ions in binding sites on the surfaces of the material. Ion exchange resins may be impregnated with particular ion species for which it has a given affinity. The ion exchange resin may be placed in an environment containing different ion species for which it has a generally higher affinity, causing the impregnated ions to leach into the environment, being replaced by the ion species originally present in the environment.

In one embodiment, a sleeve may include an ion exchange resin containing a metal ion source, such as, for example, silver. Ion exchange resins containing metal ion sources may include, for example, Alphasan® (Milliken Chemical), which is a zirconium phosphate-based ceramic ion exchange resin containing silver. An ion exchange resin may be coated onto the sleeve or it may be incorporated into the material of the sleeve.

In yet another embodiment, the sleeve may be made from natural plant materials, natural material coating or blends thereof, having inherent antimicrobial effects. Such materials include materials like bamboo, believes to possess antimicrobial activity due to some novel chitin-binding peptides.

The sleeve may be coupled to the handpiece by fitting onto the handpiece, such as, for example, by threading, friction fitting, snap fitting, and/or by any other appropriate fitting.

In some embodiments, the sleeve is snap fitted onto the handpiece. The handpiece and sleeve may thus have corresponding snap fit features or formations such that the sleeve may be securely snap-fit onto the handpiece. The snap fit may also be substantially reversible and reusable such that the sleeve may be attached, used, removed and sterilized for another use. Snap fit features or formations may include, but are not limited to, corresponding ridges and grooves, corresponding bumps and depressions, flexing snap arms and depressions, and/or any other appropriate snap fit features or formations or combinations thereof.

Most disposable prophy angles, especially commercially available ones, include both an input shaft and a driven shaft coupled to the input shaft, the input shaft is adapted for coupling to the output shaft of a handpiece via a chuck and the input shaft engaging and rotating the driven shaft via gear interfaces. The additional shaft component in the prophy angle, which is generally disposable after one patient's use, increases the amount of material wasted with the disposal of the prophy angle and also complicates certain aspects of construction as both shafts are retained in the body of the prophy angle even when not in use. This is not environmentally sound.

In the present invention, as mentioned above, the output shaft and output gear are disposed on the handpiece. In an exemplary embodiment of the invention, the handpiece includes an output shaft and an output gear, both remaining on the handpiece and being reusable. The prophy angle used with the handpiece may thus be made with only a driven shaft adapted to couple with the output gear of the handpiece for operation, such as with gear teeth, reducing the material used in the prophy angle, which is more environmentally friendly, and also simplifying aspects of the design since the prophy angle need not retain an input shaft when not in use.

As noted above, the angle has a first body having a first axial bore and a second body having a second axial bore, said second body being joined to the first body at an angle to the first body, said axial bores are in communication with each other. The first body may be adapted for attachment to a handpiece and the second body may be adapted for rotably housing a driven shaft therethrough.

In one embodiment, the angle may be about 90°. In another embodiment, the angle may be an acute angle. In yet another embodiment, the angle may be an obtuse angle.

In one embodiment of the invention, the output shaft includes a driving gear part and a driving shaft part, the gear part may include a substantially vertical surface, for example, a side face, having formations projecting perpendicularly from said face and may be arranged about its circumference. In one embodiment, the projections may be pin-like, or bullet-shaped. One example is a crown gear which generally has gear teeth projecting perpendicularly from a side face of the wheel instead of lying on the plane of the wheel.

The driven shaft also includes a driven gear disposed inside the angle body and includes a driven gear part and a driven shaft part, one end of the driven shaft part ends in the driven gear part and the other end being coupled to a prophy cup, the gear part may include a substantially horizontal surface having formations formed about the peripheral of the surface and may include depressions. The depressions of the driven gear part may include teeth, spaced apart, for meshing with the projections of the driving gear in operation. One example is a lantern gear, which generally has gear teeth in pin-shaped and lying parallel with the axis of the gear wheel. The crown and lantern gears mesh well together.

Other examples of gears may include spur gears, bevel gears and others.

In order to properly operate, the gears of the output shaft and the driven shaft mesh at a proper alignment. Since both the output shaft and driven shaft may freely rotate, they may not be at any particular position when the prophy angle is coupled to the handpiece. The dental prophylaxis device may thus incorporate a mechanism for ensuring proper meshing of the output gear and the gear teeth of the driven shaft. The proper meshing may ensure a secure attachment while in use and also be easily disengage when not in use.

In exemplary embodiments, the output shaft and/or output gear of the handpiece are spring-loaded. A spring may bias the output shaft and/or output gear distally, but may also allow movement in a proximal direction. If the initial engagement between the output gear and the gear teeth of the driven shaft is misaligned, e.g. the peaks of the teeth of each gear abut and do not mesh, the output gear may move proximally such that the prophy angle may still be attached. Upon rotation of the output shaft, the output gear may then be biased distally by the spring to properly mesh and engage the gear teeth of the driven shaft for operation when in proper alignment.

In some embodiments, the output gear may be spring-loaded on the output shaft. In other embodiments, the output shaft may be spring loaded on its coupling to the rotational source. This may be desirable as it decreases the chance of the output gear being misplaced due to a loose connection between the output gear and the output shaft at the spring-loading location.

In some embodiments, the sleeve may include formation to aid in the proper alignment of the output shaft and the driven shaft.

A prophy angle is provided for use with the handpiece, the prophy angle having a body adapted to couple to the body of the handpiece and/or the sleeve. The prophy angle may be coupled to the handpiece and/or the sleeve by fitting, such as, for example, by threading, friction fitting, snap fitting, and/or by any other appropriate fitting.

In some embodiments, the prophy angle is snap fit onto the sleeve. The prophy angle and sleeve may thus have corresponding snap fit features or formations such that the prophy angle may be securely snap-fit onto the sleeve. The snap fit may also be substantially reversible and reusable such that the prophy angle may be removed for disposal. Snap fit features or formations may include, but are not limited to, corresponding ridges and grooves, corresponding bumps and depressions, flexing snap arms and depressions, and/or any other appropriate snap fit features or formations or combinations thereof. The snap fit of the prophy angle may also serve to reinforce the fitting of the sleeve onto the handpiece by, for example, tightening around the sleeve at the snap engagement location between the sleeve and the handpiece. This may be desirable as it may help ensure the sleeve does not accidentally uncouple from the handpiece during operation.

In another aspect, the driven shaft and output gear of the handpiece include bearing surfaces. Bearing surfaces may aid in retaining proper alignment and spacing between the output gear and the driven shaft, which may aid in lowering unwanted friction between the output gear and driven shaft. In general, it may be desirable for bearing surfaces between the output gear and driven shaft to be of minimal surface area and/or such that they may slide in parallel at the contact surface rather than antiparallel. As this may reduce friction at the contact surface, it thus may aid in improving performance and/or keeping the prophy angle and/or handpiece from overheating during operation. In some embodiments, the contact surfaces only occur on one side of the center of the output gear.

In some aspects, the bearing surfaces of the driven gear and output gear may include compatibility features and/or formations. In general, it may be desirable to assure that a compatible prophy angle be utilized with the handpiece since an incompatible prophy angle may, for example, not operate properly and/or cause damage to the handpiece. Examples of compatibility features may include components of at least one of a protrusion and groove, depression or valley connection, a tongue and groove connection, and variations thereof. These compatible connections ensure easy detachment and accurate attachment between the handpiece and angle.

In one embodiment, the gear part of the output shaft may include a substantially vertical surface having projections formed thereon. The driven shaft part may include a substantially vertical portion adjacent to the gear part and having depressions formed thereon. In one aspect, a protrusion may be included on the face of the output gear which may fit into a corresponding groove of a compatible prophy angle driven shaft.

In some embodiments, a compatibility feature and/or formation may be included to substantially prevent usage of the handpiece with an incompatible prophy angle, for safety and comfort. For example, a rotational lock feature and/or formation may be included such that the rotation of the drive and/or driven shaft may be halted when the handpiece is used with an incompatible prophy angle.

In yet another aspect, the prophy angle includes features and/or formations for retaining the driven shaft independent of the driving shaft, unlike traditional prophy angles, where both the driving and driven shafts are housed in the angle and difficult to separate or disconnect. In some embodiments, the driven shaft may include at least a portion of a circumferential platform about the shaft which may be retained in the prophy angle body by a protrusion in the body. The protrusion may be hinged such that the driven shaft may be inserted into the prophy angle body freely and the hinged protrusion may be inserted to retain the driven shaft. In other embodiments, the driven shaft may include a circumferential platform with at least one section cutout. The prophy angle body may then include a protrusion which may snap past the section cutout of the platform during the insertion of the driven shaft into the prophy angle body. The protrusion may in general be larger than the section cutout such that the section cutout may deform for the protrusion to snap past.

In some embodiments, when a sleeve is used, the additional features may be formed on the angle and the sleeve for additional secure connection.

The cup has a distal end that is adapted for holding a prophylactic medium and a proximal end that is adapted for attachment to one end of the shaft part of the driven shaft. In one embodiment, the attachment of the cup may be mechanical. In another embodiment, the cup may be integrally molded onto the shaft part. In one aspect, the proximal end of the cup has a larger circumferential span than the shaft part to which it is attached and may be over-molded onto one end of the shaft part. In another aspect the proximal end of the cup has a smaller circumferential span than the shaft part. In yet another aspect, the proximal end has the same circumferential span as the shaft part. The portion of the shaft part that is covered by the proximal end of the cup may have various formations adapted for improving the attachment between the cup and the shaft part.

In some embodiments, the dental prophylaxis device also includes a foot pedal for controlling the handpiece. The foot pedal may be connected for communication with the handpiece and may include at least one actuated control for activating and deactivating the rotational source of the handpiece. The connection between the foot pedal and the handpiece may be wired or wireless. In wireless embodiments, the foot pedal may utilize any appropriate wireless connection, such as, for example, radio/microwave transmission, optical/IR transmission, ultrasonic transmission, and/or any other appropriate wireless connection. The foot pedal and handpiece may also include a syncing system such that a particular foot pedal may be associated with a particular handpiece to aid in preventing cross-talk and/or accidental activation/de-activation of other handpieces.

In one embodiment, the prophy handpiece may also be equipped with a self-contained prophylactic medium dispensing system. In general, the cup includes an aperture for a prophylactic medium to flow.

The dental prophylaxis device may further include a base station. The base station may, for example, serve as a charging base for the handpiece. The base station may thus charge the handpiece by an appropriate method, which may include, but is not limited to, inductive charging, electrical contact charging, and/or any other appropriate charging method. Inductive charging may be desirable as it does not require direct electrical contacts, which may corrode or become obstructed. In exemplary embodiments, the base station may include at least one coil with which to inductively couple to a coil in the body of the handpiece to charge the handpiece portable energy source.

The present invention together with the above and other advantages may best be understood from the following detailed description of the embodiments of the invention illustrated in the drawings.

BRIEF DESCRIPTION OF THE FIGURES

FIG. 1 illustrates dental prophylaxis device of the present invention;

FIG. 1a is an exploded view of the dental prophylaxis device of FIG. 1;

FIG. 1b shows an enlarged view of the distal end of the handpiece of the dental prophylaxis device;

FIG. 1c shows an enlarged view of the proximal end of the prophy angle of the dental prophylaxis device;

FIGS. 1d, 1e, 1f, 1g and 1h show top, bottom, front, side and back views, respectively of the handpiece with a sleeve attached;

FIGS. 1i, 1j, 1k, 1l and 1m show top, bottom, front, side and back views, respectively of the handpiece without a sleeve attached;

FIGS. 1n, 1o, 1p, 1q and 1r show top, bottom, front, side and back views, respectively of the sleeve;

FIGS. 3, 3a, 3b, 3c, 3d, 3e, 3f, 3f-1, 3g and 3h show embodiments of the interface between the output gear of the handpiece and a prophy angle;

DETAILED DESCRIPTION OF THE INVENTION

The detailed description set forth below is intended as a description of the presently exemplified device provided in accordance with aspects of the present invention and is not intended to represent the only forms in which the present invention may be practiced or utilized. It is to be understood, however, that the same or equivalent functions and components may be accomplished by different embodiments that are also intended to be encompassed within the spirit and scope of the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the exemplified methods, devices and materials are now described.

The present invention is directed to dental prophylaxis devices that improve portability, maneuverability and aid in retaining clean conditions for use on dental patients, particularly to dental handpieces. The present invention is also directed prophylaxis or prophy angles for use with such handpieces.

Figure 7:
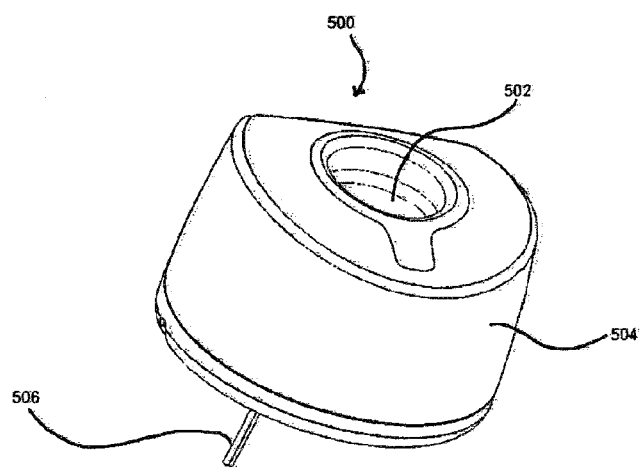
FIG. 7 illustrates a base station of the dental prophylaxis device.

In general, a dental prophylaxis device includes a handpiece 100 and a prophy angle 300, as shown in FIGS. 1 and 1a. In one embodiment, the handpiece 100 includes a body 106 having a base 101 at a proximal end 101' and an output shaft portion 104 at a distal end 103. The handpiece 100 may further include controls 108 for actuation by the user and at least one indicator 109, which may be, for example, a power indicator light. FIGS. 1i, 1j, 1k, 1l, and 1m further illustrate top, bottom, front, side, and back views, respectively, of the handpiece 100. The base 101 may also include an interface 101a, as shown in FIGS. 1e and 1j. An interface 101a may, for example, be utilized to aid docking the handpiece on a charger base 500, as shown in FIG. 7 and discussed further below. The interface 101a and the base 500 may, for example, dock with substantially corresponding features and/or formations, such as with male-female connectors. In general, a first corresponding feature or formation may be raised from the surface of either the base 101 or the base 500, such as a bump, ridge, and/or other protrusion, and a second corresponding feature or formation may be a depression in a surface, such as a socket, groove, dimple and/or other depression. Further, multiple sets of interfaces may also be utilized. The interface 101a may also be another form of retaining feature and/or formation, such as, for example, a non-slip pad, adhesive pad, magnetic retainer and/or any other appropriate retaining feature and/or formation.

In one aspect, a dental prophylaxis device also includes a sleeve 200. In one embodiment, the sleeve 200 may substantially cover a portion of the handpiece body 106 such that it may aid in isolating the handpiece 100 from the working space, such as, for example, a patient's mouth, as illustrated in the top, bottom, front, side, and bottom views of the sleeve 200 on handpiece 100 in FIGS. 1d, 1e, 1f, 1g, and 1h, respectively. This may generally aid in retaining a clean work environment by reducing the contamination of the handpiece 100 by contact with the patient's mouth and by reducing the introduction of contaminants into the patient's mouth by the handpiece 100. In general, the handpiece 100 may not be sterilizable by methods such as autoclaving due to the sensitivity of the components, such as those described in detail below. Further, the high temperature, high pressure and/or high humidity conditions of autoclaving may further contribute to wear and reduction in usage life of the handpiece 100. The sleeve 200 may thus act as a barrier and it may generally be sterilized prior to use with a patient.

The sleeve 200 may generally have the form of a hollow shell 206, as further illustrated in the top, bottom, front, side, and bottom views of the sleeve 200 in FIGS. 1n, 1o, 1p, 1q, and 1r, respectively, that may substantially surround a portion of the handpiece body 106. The sleeve 200 may also generally have a first aperture 201 for inserting the handpiece and a second aperture 203 for access between the handpiece 100 and the prophy angle 300. In some embodiments, the sleeve 200 may contour to the handpiece body 106. This may reduce the overall form size of the dental prophylaxis device and may also aid in providing ergonomic benefits to the user. The handpiece body 106 and/or the sleeve 200 may, for example, be designed for comfortable and secure gripping by a user. The sleeve 200 may also include features and/or formations 206a on the inside of the hollow shell 206, as shown in FIG. 1o. The features and/or formations 206a may, for example, aid in retaining the sleeve 200 on the handpiece body 106. The features and/or formations 206a may also, for example, space and/or cushion the sleeve 200 from the surface of the handpiece body 106. The features and/or formations 206a may be, for example, ribs, strips, pads and/or any other appropriate retainer, spacer, and/or cushioning.

In general, the sleeve 200 may be constructed from a sterilizable and reusable material or combination of materials. Appropriate materials may include, but are not limited to, polymers such as polyetherimides, polycarbonates, acrylics, acetals, polyetheretherketones (PEEK), polypropylenes and polyethylenes, metals such as aluminum, titanium, stainless steel and silver, composite materials such as fiberglass and carbon fiber reinforced plastics, and/or any other appropriate material. The material may generally be autoclavable and reusable for at least a given number of normal use and sterilization cycles. In an exemplary embodiment, the sleeve is made from polyetherimide polymer such as ULTEM® Resin (GE Plastics).

The handpiece body 106 may also be constructed of similar material as those used in the manufacture of the sleeve 200, as well as other materials that may not be sterilizable or autoclavable.

In some embodiments, the sleeve 200 and/or handpiece 100 may include coatings capable of eliminating, preventing, retarding or minimizing the growth of microbes, thus minimizing the use of high temperature autoclaving process or harsh chemicals and may increase the kind and number of materials useful as substrates for making such tools or instruments.

As mentioned before, the coatings may include chemical anti-microbial materials or compounds that are capable of being substantially permanently bonded, at least for a period such as the useful life sleeve, or maintain their anti-microbial effects when coated with the aid of coating agents, onto the exposed surfaces of the sleeve. In one example, the chemicals may be deposited on the surface of the sleeve by covalent linkage.

These covalently bonded materials may act to minimize microbial growth on the sleeve or handpiece, tongue scraper 11, either disposable or reusable. In addition, any microbial organisms that may chance to be attached to the material may be killed by interaction with the coating. For example, quaternary ammonium cations, such as N-alkyl-pyridiniums, may be used as antimicrobial moieties in covalently attached polymeric surface coatings. In one embodiment, poly(4-vinyl-N-hexylpyridinium) (N-alkylated-PVP) is noted to have an optimum alkyl side chain length for antimicrobial activity. The side chain length of the alkyl group may, for example, vary from 0 (to side chain) to 12 carbons long, more for example from 5 to 7 carbons long. The alkyl side chains may provide increased hydrophobicity for the coating and may promote association with microbial membranes. Polyethylenimine (PEI) may be also used as a bacteriocidal coating when both N-alkylated on its primary amino group and subsequently N-methylated on its secondary and tertiary amino groups to raise the overall number of cationic quaternary amino groups. An increased number of cationic groups (permanently charged or charged due to the pH of the system) may promote an electrophoretic mechanism when associated with microbial membranes, which may promote the lysis of the microbe. Any such covalently bonded quaternary ammonium cation polymeric coatings may be used to give an antimicrobial property to the tongue scraper surface.

Antimicrobial coatings may be covalently attached to the surface by a variety of methods and may include, for example, creating suitable reaction sites, such as free hydroxyl or amino groups, by coronal discharge, surface etching, hydrolyzation or other methods that disrupt the surface of the sleeve 200 and/or handpiece 100 to create sites of suitable reactivity. The antimicrobial coatings may then be synthesized by reacting the various precursors with the prepared surface of the sleeve 200 and/or handpiece 100 to build the proper coating. In other cases, silanes may be used as coupling agents to complex antimicrobial moieties to the surface of the sleeve 200 and/or handpiece 100.

In other embodiments, the coatings may include chemical antimicrobial materials or compounds that may be deposited in a non-permanent manner such that they may dissolve, leach or otherwise deliver antimicrobial substances to a useful field, such as the mouth, during use.

In still other embodiments, the coatings may include sources of anti-microbial agents which may leach and/or release agents in a moist environment or upon contact with moisture. These sources may be incorporated into the substrate materials used for manufacturing the sleeve, or included in the coatings coated on the exposed surfaces of the sleeve. Incorporation of the sources is especially suited to polymeric substrates.

In addition to above, chemical antimicrobial materials or compounds may include a variety of substances including, but not limited to antibiotics, antimycotics, general antimicrobial agents, metal ion generating materials, or any other materials capable of generating an antimicrobial effect. Chemical antimicrobial materials or compounds may also be selected to, for example, minimize any adverse effects or discomfort to the patient.

The anti-microbial compound may include, but are not limited to, antibiotics, quaternary ammonium cations, a source of metal ions, triclosan, chlorhexidine, and/or any other appropriate compound or mixtures thereof.

In yet further embodiments, as also mentioned above, antimicrobial activity may be achieved by utilizing the antimicrobial properties of various metals, especially transition metals which have little to no effect on humans. Examples may include sources of free silver ions, which are noted for their antimicrobial effects and few biological effects on humans. Metal ion antimicrobial activity may be created by a variety of methods that may include, for example, mixing a source of a metal ion with the material of a dental instrument during manufacture, coating the surface by methods such as plasma deposition, loosely complexing the metal ion source by disrupting the surface of the dental instrument to form affinity or binding sites by methods such as etching or coronal discharge, and depositing a metal onto the surface by means such as electroplating, photoreduction and precipitation. The sleeve surface may then slowly release free metal ions during use that may produce an antimicrobial effect.

In some embodiments, the source of metal ions may be an ion exchange resin. Ion exchange resins are substances that carry ions in binding sites on the surfaces of the material. Ion exchange resins may be impregnated with particular ion species for which it has a given affinity. The ion exchange resin may be placed in an environment containing different ion species for which it has a generally higher affinity, causing the impregnated ions to leach into the environment, being replaced by the ion species originally present in the environment.

In one embodiment, a sleeve may include an ion exchange resin containing a metal ion source, such as, for example, silver. Ion exchange resins containing metal ion sources may include, for example, Alphasan® (Milliken Chemical), which is a zirconium phosphate-based ceramic ion exchange resin containing silver. An ion exchange resin may be coated onto the sleeve or it may be incorporated into the material of the sleeve.

In yet another embodiment, as mentioned above, natural plant materials like bamboo, having antimicrobial effects, may be used in the manufacturing of the sleeve 200 and/or handpiece 100. These plant materials are believed to have inherent antimicrobial effects. Such materials, such as bamboo, are believed to possess antimicrobial activity due to some novel chitin-binding peptides, such as those designated Pp-AMP 1 and Pp-AMP 2, which had antimicrobial activity against pathogenic bacteria and fungi, purified from Japanese bamboo shoots (*Phyllostachys pubescens*) (See Bioscience, Biotechnology, and Biochemistry, Vol. 69 (2005), Vol. 3, pp 643-645, the entire contents of which are incorporated herein by reference).

In one aspect, the plant material may be used for the manufacturing of the sleeve 200 and/or handpiece 100. In another aspect, the plant material maybe incorporated in the polymeric materials used in the manufacturing of the sleeves 200 and/handpiece 100. In yet another aspect, the natural plant material may be coated as a coating on the surface of the sleeves 200 and/handpiece 100. In still another aspect, the coating of the natural plant material maybe blend with a coating agent for better adhesion onto the surface of the sleeves 200 and/handpiece 100 thereof.

The sleeve 200 may be coupled to the handpiece 100 by fitting onto the handpiece body 106, such as, for example, by threading, friction fitting, snap fitting, and/or by any other appropriate fitting.

In some embodiments, the sleeve 200 is snap fit onto the handpiece 100. FIG. 1a shows an exploded view of the handpiece 100, sleeve 200 and prophy angle 300. The handpiece 100 and sleeve 200 may thus have corresponding snap fit features or formations such that the sleeve 200 may be securely snap fit onto the handpiece 100. The snap fit may also be substantially reversible and reusable such that the sleeve 200 may be attached, used, removed and sterilized for another use. Snap fit features or formations may include, but are not limited to, corresponding ridges and grooves, protrusions and depressions or grooves, corresponding bumps and depressions, flexing snap arms and depressions, and/or any other appropriate snap fit features or formations or combinations thereof, to be described in more detail below.

For example, the sleeve 200 may fit over the handpiece 100 in such a manner as to reduce significant rotation of the sleeve 200 with respect to the handpiece body 106. In one embodiment, the connection may include the components of a bayonet type connection disposed in the sleeve 200 and the handpiece body 106. The connection may also include the components of tongue and groove type connections, internesting pin and pinhole connections, latches, clips and any other interconnecting structure configured to minimize significant rotation of the sleeve 200 with respect to the handpiece 100 during operation of the handpiece. This may also extend to the connection between the prophy angle 300 and the sleeve 200 and/or the handpiece 100.

FIG. 1a illustrates an embodiment of a sleeve 200 which includes a rotational lock cutout form 201a which may abut against housing formation 106a to prevent rotation of the sleeve 200 about the handpiece 100. FIGS. 1b and 1c illustrate a similar rotational lock cutout form 305a of prophy angle 300 which may abut against sleeve formation 202a to prevent or minimize rotation of the prophy angle 300 about the sleeve 200. A second rotational lock cutout form 201b, as shown in FIGS. 1n, 1o, 1p and 1q, may also be utilized to abut against a housing formation 106b, as shown in FIG. 1h.

In the illustrated embodiment, the sleeve 200 includes snap fit arms 205 with protrusions 207, while the handpiece 100 includes a corresponding groove 107 on snap fit section 105. The handpiece 100 may be inserted into the sleeve 200 through aperture 201. The snap fit arms 205 may then flex as the snap fit section 105 and output shaft section 104 of the handpiece 100 pass through aperture 203 until the protrusions 207 snap into the groove 107, which may substantially lock the sleeve 200 onto the handpiece 100. It may be appreciated that the flexibility of the snap fit arms 205 and the design of the protrusions 207 and groove 107 may contribute to the stability of the retention of the sleeve 200 on the handpiece 100 as well as the ease with which the sleeve 200 may be removed.

The prophy angle 300 generally includes a body 304 and a head portion 302 from which a prophy cup 310 extends. In one aspect, the prophy angle 300 is adapted to couple to the handpiece body 106 and/or the sleeve 200. The prophy angle 300 may be coupled to the handpiece 100 and/or the sleeve 200 by fitting, such as, for example, by threading, friction fitting, snap fitting, and/or by any other appropriate fitting.

In some embodiments, the prophy angle 300 is snap fit onto the sleeve 200. The prophy angle 300 and sleeve 200 may thus have corresponding snap fit features or formations such that the prophy angle 300 may be securely snap fit onto the sleeve 200. The snap fit may also be substantially reversible and reusable such that the prophy angle 300 may be removed. Snap fit features or formations may include, but are not limited to, corresponding ridges and grooves, corresponding bumps and depressions, flexing snap arms and depressions, and/or any other appropriate snap fit features or formations or combinations thereof. The snap fit of the prophy angle 300 may also serve to reinforce the fitting of the sleeve 200 onto the handpiece 100 by, for example, tightening around the sleeve 200 at the snap engagement location between the sleeve 200 and the handpiece 100. This may be desirable as it may help ensure the sleeve 200 does not accidentally uncouple from the handpiece 100 during operation.

FIGS. 1a, 1b and 1c illustrate the snap fit between the prophy angle 300 and the sleeve 200. The sleeve 200 may include protrusions 202 which may snap past a ridge 307 on the inner surface of the prophy angle snap fit portion 305. For attachment, the sleeve 200 and the handpiece 100 may be inserted into the aperture 301 of the prophy angle 300 until the protrusions 202 snap past the ridge 307, which may substantially lock the prophy angle 300 to the sleeve 200. It may be appreciated that the flexibility of the snap fit portion 305 and the design of the protrusions 202 and ridge 307 may contribute to the stability of the retention of the prophy angle 300 on the sleeve 200 as well as the ease with which the prophy angle 300 may be removed.

Figure 2:
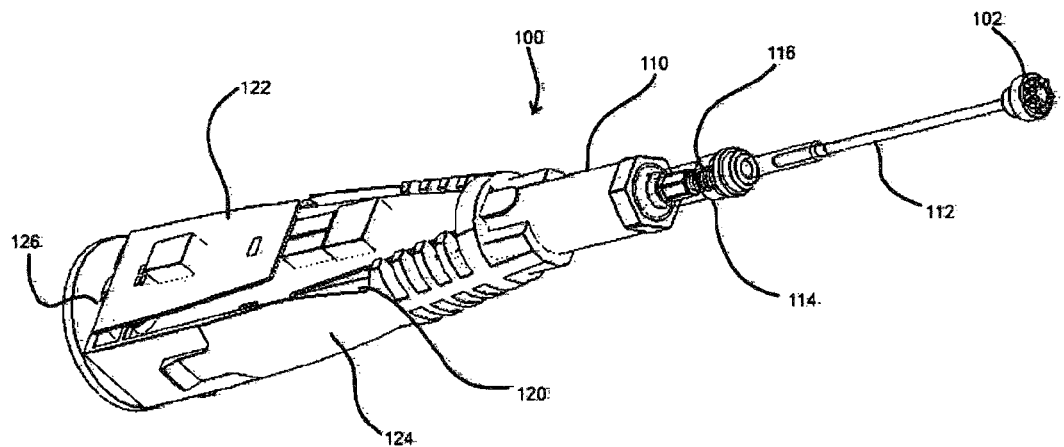
FIG. 2 illustrates the internal components of handpiece.

As illustrated in FIG. 2, the handpiece 100 houses a rotational source 110 coupled to an output shaft 112. The handpiece 100 may further include other components such as, for example, control circuitry 122, user controls, indicators, and/or any other appropriate components. The components may be supported by a chassis 124 in the handpiece 100. In general operation, the user actuates a control 108, such as shown in FIGS. 1 and 1a, to activate the rotational source 110 to rotate the output shaft 112. The rotational source 110 may utilize a transmission 114 which may be utilized to change the rotational speed produced by the rotational source 110. The transmission 114 may, for example, include a gear reduction mechanism. The rotational source 110 may, for example, be an electrically powered motor. The rotational source 110 is generally powered by a portable energy source 120, such as a battery, capacitor and/or combinations thereof. The portable energy source 120 may generally be disposed in the housing 106 of the handpiece 100 or be attached thereto.

Figure 3:
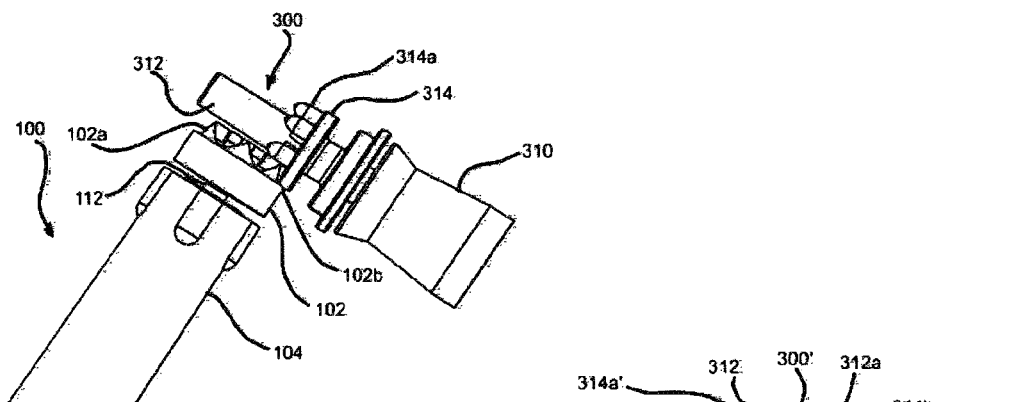

In general, the output shaft 112 couples to a driven shaft 312 in the prophy angle 300 via an output gear 102, as illustrated in FIG. 3. The output gear 102 transmits the rotation of the output shaft 112 to the driven shaft 312 via angled gear interfaces 102a, 314a on the output gear 102 and driven shaft 312, respectively, which in turn rotates the prophy cup 310 for cleaning and/or polishing action on the teeth of a patient. Generally, the output gear 102 and the gear interfaces on the driven shaft 312 may be any appropriate set of interfacing gears, which may include, but are not limited to, crown and spur gears, spur to spur gears, crown and lantern gears, crown to crown gears, helical gears, and/or any other appropriate interfacing gear set.

In another aspect, the output shaft 112 and output gear 102 are disposed on the handpiece 100, unlike most disposable prophy angles which include both an input shaft and a driven shaft, the input shaft coupling to the output shaft of a handpiece via a chuck and the input shaft engaging and rotating the driven shaft via gear interfaces. As noted above, the additional shaft component of most disposable prophy angles increases the amount of material wasted with the disposal of the prophy angle and also complicates certain aspects of construction as both shafts are retained in the body of the prophy angle even when not in use. These have led to some elaborate mounting and retention devices for prior art angles.

In an exemplary embodiment, the handpiece 100 includes an output shaft 112 and an output gear 102, both remaining on the handpiece 100 and being reusable. The output shaft 112 may be housed within the output shaft portion 104 of the handpiece body 106. The prophy angle 300 used with the handpiece 100 may thus have only a driven shaft 312 adapted to couple with the output gear 102 of the handpiece 100 for operation, reducing the material used in the prophy angle 300 and also simplifying aspects of the design since the prophy angle 300 need not retain an input shaft.

To properly operate, the gear interfaces 102a, 314a of the output gear 102 of the output shaft 112 and the driven shaft 312, respectively, mesh at a proper alignment when the angle 300 is mated to or mounted on the handpiece 100. Since both the output shaft 112 and driven shaft 312 may freely rotate, they may not be at any particular position when the prophy angle 300 is coupled to the handpiece 100. The dental prophylaxis device may thus incorporate a mechanism for ensuring proper meshing of the output gear 102 and the gear teeth 314a of the driven shaft 312 during use.

In exemplary embodiments, the output shaft 112 and/or the output gear 102 of the handpiece 100 are spring-loaded. A spring 116 may bias the output shaft 112 and/or output gear 102 distally, but may also allow movement in a proximal direction. If the initial engagement between the output gear 102 and the gear teeth 314a of the driven shaft 312 is misaligned, e.g. the peaks of the teeth of each gear abut and do not mesh, the output gear 102 may move proximally such that the prophy angle 300 may still be attached. Upon rotation of the output shaft 112, the output gear 102 may then be biased distally by the spring 116 to properly mesh and engage the gear teeth 314a of the driven shaft 312 for operation when in proper alignment.

In some embodiments, the output gear 102 may be spring-loaded on the output shaft 112. In other embodiments, the output shaft 112 may be spring loaded on its coupling to the rotational source 110. This may be desirable as it decreases the chance of the output gear 102 being misplaced due to a loose connection between the output gear 102 and the output shaft 112 at the spring-loading location.

In another aspect, the driven shaft 312 and output gear 102 of the handpiece 100 include bearing surfaces. Bearing surfaces may aid in retaining proper alignment and spacing between the output gear 102 and the driven shaft 312, which may aid in lowering unwanted friction between the output gear 102 and driven shaft 312. In general, it may be desirable for bearing surfaces between the output gear 102 and driven shaft 312 to be of minimal surface area and/or such that they slide in parallel at the contact surface rather than antiparallel. This may reduce friction at the contact surface and thus may aid in improving performance and/or keeping the prophy angle 300 from overheating during operation. In some embodiments, the contact surfaces only occur on one side of the center of the output gear 102.

Figure 3A:
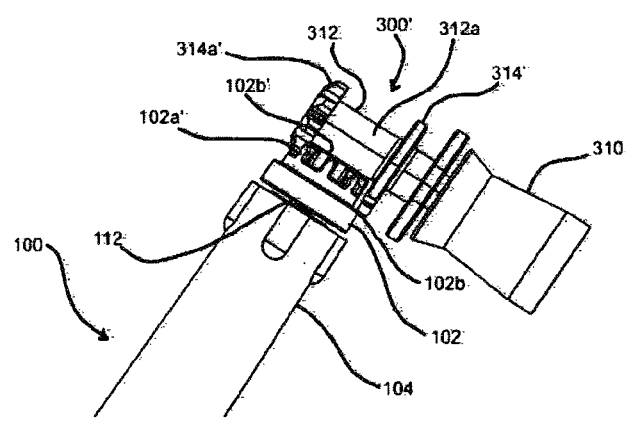
Figure 3G:
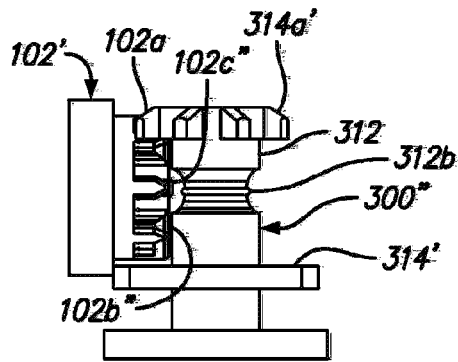

FIG. 3 illustrates an embodiment of a prophy angle 300 and output gear 102 of a handpiece 100. The output gear 102 includes gear teeth 102a and a bearing surface 102b which contacts the driven shaft 312 at a bearing surface 314 in a parallel sliding manner. The gear teeth 314a of the driven shaft 312 may, as shown, extend from the bearing surface 314. In another embodiment, gear teeth 314a' may also extend directly from the driven shaft 312, as shown in the prophy angle 300' of FIG. 3a. The output gear 102 may contact the driven shaft 312 via bearing surfaces 102b, 314' or it may also abut against the driven shaft surface 312a with output gear surface 102b'.

In still another embodiment, a prophy angle 300" may include a bearing contact 102c which may extend from the output gear surface 102b" of the output gear 102', as illustrated in FIG. 3b. The driven shaft 312 of the prophy angle 300" may include a bearing groove 312b which may contact the bearing contact 102c of the output gear 102'. This contact may aid in the vertical alignment of the gear teeth 102a of the output gear 102' with the gear teeth 314a' of the driven shaft 312. The distance between the output gear 102' and the driven shaft 312 may also be set by the bearing contact 102c and the bearing groove 312b such that the output gear surface 102b" does not contact the driven shaft 312.

In an exemplary embodiment, as shown in FIG. 3c, the bearing contact 102c only contacts the bearing groove 312b with portion 102d along only a portion 312c of the bearing groove 312b such that the contact slides in a parallel manner.

In another exemplary embodiment, as shown in FIGS. 3d and 3e, the output gear 102" may include a bearing surface 102c' which may bear against a bearing surface 312b' of driven shaft 312 of a prophy angle 300". The bearing may also serve to prevent or minimize the output gear 102" from advancing distally such that it does not abut against the driven shaft 312 on a non-bearing surface.

Figure 3H:
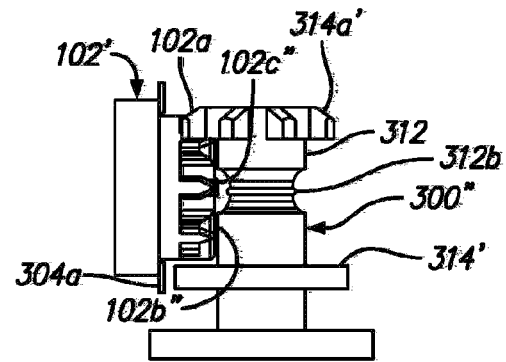

Other features or formations may also be utilized to prevent the output gear from advancing distally, such as formations in the bore of the prophy angle body, an example of which is shown with formations 304a in FIG. 3h.

In some aspects, the prophy angle and output gear may include compatibility features and/or formations. In general, it may be desirable to assure that a compatible prophy angle be utilized with the handpiece 100 since an incompatible prophy angle may, for example, not operate properly and/or cause damage to the handpiece. In some embodiments, a protrusion may be included on the face of the output gear which may fit into a corresponding groove of a compatible prophy angle driven shaft.

FIGS. 3b, 3c, 3d and 3g illustrate embodiments where a protrusion in the output gear fits into a corresponding groove in the driven shaft to aid in ensuring use of a compatible prophy angle. The protrusion may contact the groove in particular manner to ensure parallel sliding, such as with the bearings 102c and 102c' of FIGS. 3b and 3d, respectively. The protrusion may also be a non-contact fit, such as with the protrusion 102c" of FIG. 3g. Incompatible prophy angles may, for example, contact the protrusion in an undesirable manner and generate friction and/or noise. The contact with the protrusion may also, for example, result in the prophy angle not fitting properly onto the handpiece.

In other embodiments, a compatibility feature and/or formation may be included to substantially prevent usage of the handpiece with an incompatible prophy angle. For example, a rotational lock feature and/or formation may be included such that the rotation of the drive and/or driven shaft may be halted when the handpiece is used with an incompatible prophy angle. In one embodiment, an output gear may include a groove, such as the groove 102e of output gear 102" of FIGS. 3d, 3e and 3f. The groove 102e may be, for example, a semi-cylindrical groove which, when used with an incompatible prophy angle, may lock the driven shaft 312-1 of the incompatible angle, as shown in FIGS. 3f and 3f-1, due to the output gear 102" being spring-loaded and biased distally 313a toward the driven shaft 312-1. In an initial configuration, as shown in FIG. 3f-1, the absence of a surface for bearing 102c' to abut may cause the clearance 313 to decrease due to the spring bias 313a until the surface of the gear 102" abuts the driven shaft 312-1 of the incompatible angle. As the gear 102" rotates, the semi-cylindrical groove 102e may rotate into curvature alignment with the surface of the driven shaft 312-1 until the spring bias 313a may push the driven shaft 312-1 into the groove 102e, locking it in place as shown in FIG. 3f. This may substantially prevent the usage of the incompatible prophy angle as rotation may be prevented. A compatible prophy angle, such as the prophy angle 300" of FIG. 3d, may still operate as the bearings 102c' and 312b' substantially prevent the output gear 102" from moving distally into the clearance space 313 and locking onto the driven shaft 312 in the groove 312b. It may be appreciated that the compatibility features may also be utilized with any appropriate interfacing gear sets, as discussed above.

Figure 4:
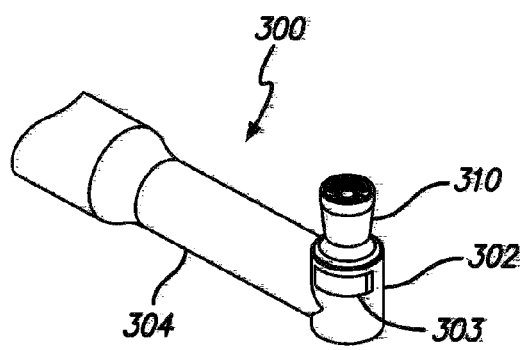
FIGS. 4, 4a and 4b illustrate a prophy angle with a hinged protrusion retaining a driven shaft.
Figure 4A:
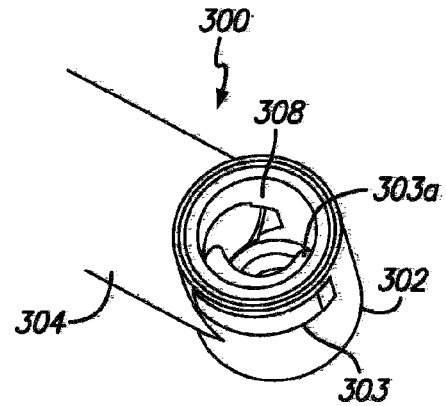
Figure 4B:
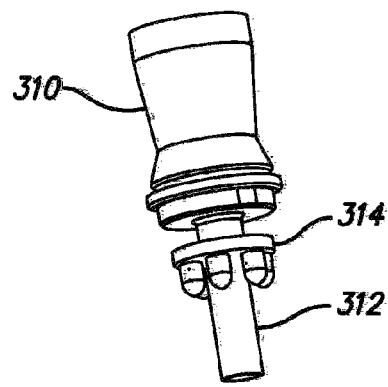

In yet another aspect, the prophy angle includes features and/or formations for retaining the driven shaft. In some embodiments, as shown in FIGS. 4, 4a and 4b, the driven shaft 312 of the prophy angle 300 may include at least a portion of a circumferential platform 314, which may also be the bearing surface as described above, about the shaft 312 which may be retained in the prophy angle body 304 by a protrusion 303 in the head portion 302. The protrusion 303 may be hinged such that the driven shaft 312 may be inserted into the prophy angle head 302 via aperture 308 freely and the hinged protrusion 303 may be inserted to retain the driven shaft 312, with portion 303a contacting the platform 314.

In other embodiments, as shown in the prophy angle 300" of FIGS. 5, 5a, 5b and 5c, the driven shaft 312 may include a circumferential platform 314 with at least one section cutout 314b. The prophy angle head 302 may then include a protrusion 320 at the aperture 308 which may snap past the section cutout 314b of the platform 314 during the insertion of the driven shaft 312 into the aperture 308. The protrusion 320 may in general be larger that the section cutout 314b such that the section cutout 314b deforms for the protrusion 320 to snap past. Additional cutouts 314c may be included adjacent to the cutout 314b such that the portions 314d may more easily flex to allow the protrusion 320 to snap past.

Figure 5:
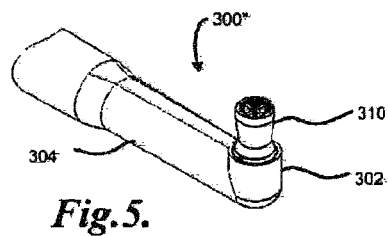
FIGS. 5, 5a, 5b and 5c illustrate a prophy angle with a snap past retention of a driven shaft.
Figure 5A:
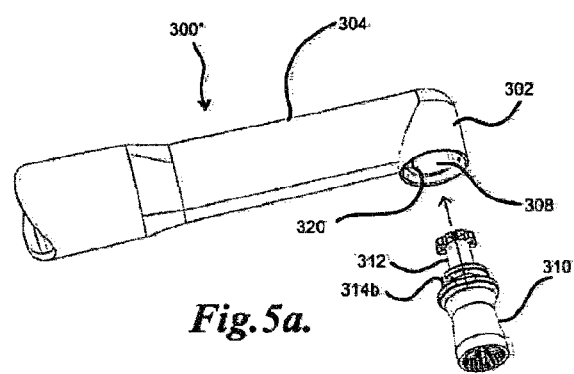
Figure 5B:
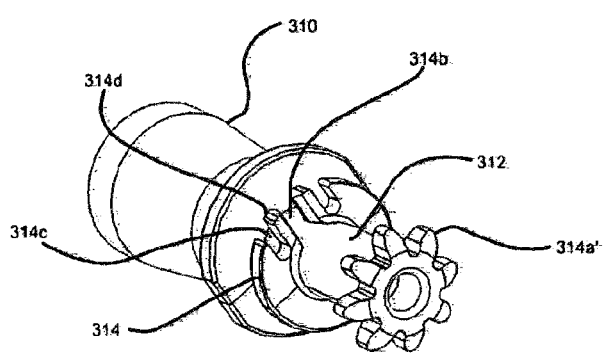
Figure 5C:
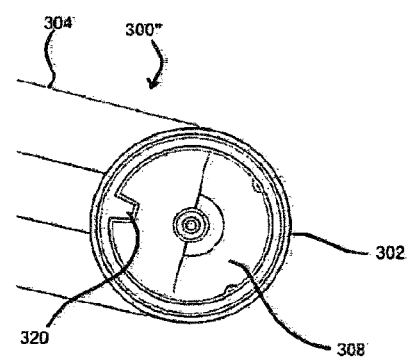

As mentioned above, a cup 310 may be attached to the prophy angle 300 or 300", as shown in FIG. 4 or 5, for use in polishing a tooth or teeth. The cup 310 has a distal end that is adapted for holding a prophylactic medium (not shown) and a proximal end that is adapted for attachment to one end of the shaft part 312.

The cup 310 has a housing formed of a resilient material such an elastomeric polymer. The cup 310 may be substantially rotationally symmetrical about a first longitudinal axis (not shown) and be coupled to the shaft part 312, which may be part of a drive mechanism. The cup 310 may be attached to the driven shaft part 312 in a variety of attachment methods, including, for example, a snap-on attachment, a co-molded attachment, or an over-molded attachment method. The shaft part 312 may also include some formations or coupling features 510, an embodiment of which is exemplified in FIG. 8.

Figure 8:
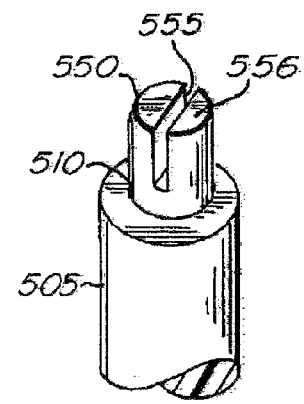
FIG. 8 shows, in perspective view, an embodiment of a prophy cup coupling feature for a prophy angle driven shaft according to various embodiments of the invention.

In one embodiment, the cup 310 may be integrally molded onto the shaft part 312. In one aspect, the proximal end of the cup 310 has a larger circumferential span than the shaft part 3 to which it is attached and may be over-molded onto one end of the shaft part 312, as shown in FIG. 8. In another aspect the proximal end of the cup 310 has a smaller circumferential span than the shaft part 312. In yet another aspect, the proximal end has the same circumferential span as the shaft part 312. The portion of the shaft part 312 that is covered by the proximal end of the cup 310 may have various formations adapted for improving the attachment between the cup 310 and the shaft part 312. Details of the formations and features are found in co-pending U.S. patent application Ser. No. 11/376,466, the contents of which are hereby incorporated by reference.

FIG. 8 is a perspective view of one exemplary embodiment of the coupling feature 510 where the coupling feature 510 is substantially a cylinder 550 positioned substantially coaxially with the cup 310 when mounted or attached to the shaft part 312. The shaft part may have two portions 510 and 505 having different circumferential span or diameters. The cylinder 550 may have a diametric notch 555 extending partially inward from a distal surface 556 of the coupling feature 510 toward the portion 505. In this embodiment, the formation or coupling feature may be in the shape of a slot when view from the end of the shaft part 312.

The material used for forming the cup 310 may fill in the slot formation and improve the anchoring strength between the cup 310 and the shaft part 312, in the embodiments where the cup 310 is over-molded or the embodiments where the cup 310 is not over-molded onto the shaft part 312.

The structures, one of which is shown in FIG. 8, present more bonding surfaces for the material used for forming the cup to improve the anchoring strength between the cup 310 and the shaft part 312, in the embodiments where the cup 310 is over-molded or the embodiments where the cup 310 is not over-molded onto the shaft part 312.

The term "over-molding" as used herein refers to the molding of the cup 310 around or onto a pre-formed shaft part 312. In some embodiments, during molding of the cup 310, parts of the shaft part 312 in contact with the material forming the cup 310 may become softened or slightly melted, causing a co-mingling of the materials to form a stronger bond. In other embodiments, there is no softening or melting of the shaft part 312, and the cup material merely forms about the formations 510 and/or seeps into the holes in the formations 510. In still other embodiments, both the co-mingling and forming about the formations may happen.

In one embodiment of the invention, a reinforcing material may be placed through the through-holes, if one is present in the structure. This reinforcing material may serve to strengthen the polymeric material used in the construction of the cup 310, and further improve the ability of the prophy cup 310 to remain attached to the driven shaft 312 during loading of the cup 310 with polishing paste and polishing of teeth. In various embodiments, the reinforcing material may include organic fibers such as, for example, polyaramid (Kevlar®) fibers and inorganic fibers such as, for example, glass or carbon fibers. In another embodiment, the reinforcing material may include a solid member of a polymer material, a metallic material, or other shear-resistant material. In still another embodiment, the reinforcing material may include a miniature multi-stranded cable formed, for example, of stainless steel and/or titanium. In still another embodiment, the lateral reinforcing material may include a linked member, such as a chain of polymer links, metallic links, or links of other appropriate material.

In one embodiment, the prophy handpiece 300 or 300" may also be equipped with a self-contained prophylactic medium dispensing system. In general, the cup 310 includes an aperture for a prophylactic medium to flow. Details of a self-contained dispensing system may be found in U.S. provisional application Ser. No. 60/889,733 and U.S. patent publication No. 2006/0127844, the entire contents of which are both hereby incorporated by reference.

Figure 6:
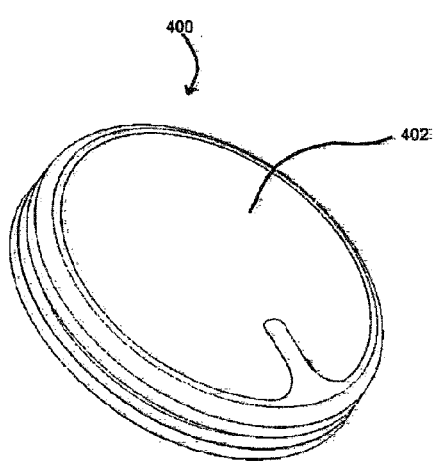
FIGS. 6 and 6a illustrate a foot pedal of the dental prophylaxis device.
Figure 6A:
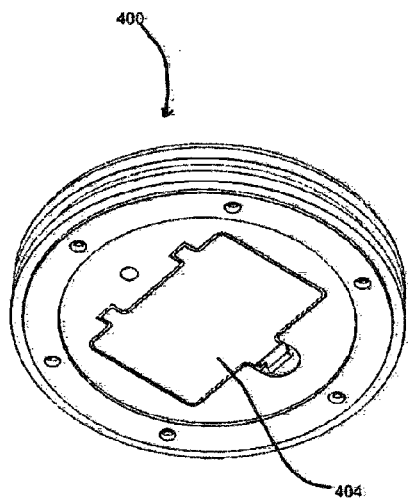

In some embodiments, the dental prophylaxis device also includes a foot pedal 400 for controlling the handpiece 100, as shown in FIGS. 6 and 6a. The foot pedal 400 may be connected for communication with the handpiece 100 and may include at least one actuated control 402 for activating and deactivating the rotational source 110 of the handpiece 100. The connection between the foot pedal 400 and the handpiece 100 may be wired or wireless. In wireless embodiments, the foot pedal 400 may utilize any appropriate wireless connection, such as, for example, radio/microwave transmission, optical/IR transmission, ultrasonic transmission, and/or any other appropriate wireless connection. The foot pedal 400 and handpiece 100 may also include a syncing system such that a particular foot pedal may be associated with a particular handpiece to aid in preventing cross-talk and/or accidental activation/deactivation of other handpieces. The foot pedal 400 may further include a portable energy source, such as a battery, which may be internal to the foot pedal 400 and may be retained in a power source portion 404. Details of a wireless control system may be found in co-pending U.S. patent application Ser. No. 11/417,284, the entire contents of which are hereby incorporated by reference.

The dental prophylaxis device may further include a base station 500, as shown in FIG. 7. The base station 500 may, for example, serve as a charging base for the handpiece 100. The base station 500 may thus include a receptacle 502 for the base portion 101 of the handpiece 100. The base station 500 may thus charge the handpiece 100 by an appropriate method, which may include, but is not limited to, inductive charging, electrical contact charging, and/or any other appropriate charging method. Inductive charging may be desirable as it does not require direct electrical contacts, which may corrode or become obstructed. In exemplary embodiments, the base station 500 may include at least one coil within the body 504 near or about the receptacle 502 with which to inductively couple to a coil in the base 101 of the handpiece 100 to charge the handpiece portable energy source 120. The base station 500 may further include a power line 506 for attachment to a power source, such as an electrical outlet.

While exemplified embodiments of the invention have been described and illustrated above, it should be understood that these are exemplary of the invention and are not to be considered as limiting. Accordingly, the invention is not to be considered as limited by the foregoing description, but is only limited by the scope of the claims appended hereto.

What is claimed is:

1. A dental prophylaxis device comprising:
a handpiece having a body;
a removable hollow shell surrounding said body;
an electric motor mounted inside said body;
said electric motor coupled to an output shaft;
said output shaft comprising a driving shaft part and an output gear, said output gear having a substantially vertical surface comprising formations on said surface; and
a prophy angle removably coupled to said handpiece and said hollow shell and comprising an axial bore having a driven shaft;
said driven shaft including a shaft part having two ends, one end ending in a driven gear part and the other end having a prophy cup attached thereon for rotation thereto, said shaft part comprising formations;
wherein said electric motor couples to the driven shaft of the prophy angle via the formations on said output gear and the shaft part, said formations on said output gear and the shaft part comprising complementary formations for easy detachment and accurate attachment of the output and driven shafts, and wherein the shell includes a first aperture for inserting the handpiece body into the shell and a second aperture for receiving the output shaft therethrough when the prophy angle is removed from the body, wherein the shell further includes a plurality of circumferentially arranged snap fit arms extending therefrom that include protrusions thereon that are received in a corresponding groove defined in the handpiece, and wherein the snap fit arms extend from the shell into the axial bore of the prophy angle.

2. The dental prophylaxis device of claim 1 wherein said complementary formations comprises the components of at least one of a protrusion and groove or valley connection or a tongue and groove connection.

3. The dental prophylaxis device of claim 1 wherein:
said substantially vertical surface further comprises said formations about the periphery of said surface; and
said driven gear part is disposed inside said axial bore of said angle, wherein said driven gear part comprises a substantially horizontal surface having formations extending from about the periphery of said substantially horizontal surface;
wherein said formations on said substantially vertical surface and said formations on said substantially horizontal surface mate cooperatively during use.

4. The dental prophylaxis device of claim 3 wherein said formations on said substantially vertical surface and said formations on said substantially horizontal surface comprises crown and lantern gears, rack and pinion gears, crown and spur gears, spur to spur gears, crown to crown gears or helical gears.

5. The dental prophylaxis device of claim 3 wherein said output gear is spring-loaded.

6. The dental prophylaxis device of claim 3 further comprising a spring for biasing said output gear distally while allowing movement in a proximal direction to provide better mating between the driven shaft and the output shaft during coupling of said shafts.

7. The dental prophylaxis device of claim 3 wherein said driven shaft is spring-loaded.

8. The dental prophylaxis device of claim 1 wherein said hollow shell surrounds a portion of the handpiece body and covers a portion of the handpiece for isolating the handpiece from a working space.

9. The dental prophylaxis device of claim 8 wherein said hollow shell further comprises formations for coupling to the angle.

10. The dental prophylaxis device of claim 8 wherein said hollow shell is removably coupled to said handpiece body in an anti-rotational manner.

11. The dental prophylaxis device of claim 1 wherein said body of said handpiece comprises an antimicrobial coating.

12. The dental prophylaxis device of claim 1 wherein said shell is contoured to said handpiece body for gripping by a user.

13. The dental prophylaxis device of claim 1 wherein the prophy angle includes a ridge on an inside surface thereof, wherein the shell includes protrusions extending outwardly therefrom, and wherein the ridge on the prophy angle and the protrusions on the shell are in a snap fit relationship.

* * * * *